US005744337A

United States Patent [19]

Price et al.

[11] Patent Number: 5,744,337
[45] Date of Patent: Apr. 28, 1998

[54] INTERNAL GELATION METHOD FOR FORMING MULTILAYER MICROSPHERES AND PRODUCT THEREOF

[75] Inventors: Ronald R. Price, Stevensville; Mariam Monshipouri, Bethesda, both of Md.

[73] Assignee: The United States of America as represented by the Secretary of the Navy, Washington, D.C.

[21] Appl. No.: 587,798

[22] Filed: Dec. 26, 1995

[51] Int. Cl.$^6$ .................. C12N 11/10; A23L 1/0532; B01J 13/18

[52] U.S. Cl. .................. 435/178; 264/4.3; 264/4.32; 264/4.7; 426/534; 426/573; 435/262.5; 435/821

[58] Field of Search .................. 264/4.3, 4.32, 264/4.7; 435/178, 821; 426/534, 573

[56] References Cited

U.S. PATENT DOCUMENTS

| | | | |
|---|---|---|---|
| 3,819,838 | 6/1974 | Smith et al. | 426/89 |
| 3,970,594 | 7/1976 | Claybaugh | 510/438 |
| 4,563,366 | 1/1986 | Baird et al. | 426/573 |
| 4,621,040 | 11/1986 | Viola | 430/138 |
| 4,647,536 | 3/1987 | Mosbach et al. | 435/178 X |
| 4,822,534 | 4/1989 | Lencki et al. | 264/4.3 |
| 4,923,645 | 5/1990 | Tsang et al. | 264/4.3 |
| 4,996,150 | 2/1991 | Joung et al. | 435/178 X |
| 5,093,253 | 3/1992 | Nolan | 435/178 |
| 5,175,093 | 12/1992 | Seifert | 435/178 X |
| 5,427,935 | 6/1995 | Wang et al. | 435/178 |

OTHER PUBLICATIONS

Kondo:*Microcapsule Processing and Technology*, Marcel Dekker, Inc., New York (1979) p. 118. [TS 198.C33K6613].

*Primary Examiner*—Richard D. Lovering
*Attorney, Agent, or Firm*—Thomas E. McDonnell; Barry Edelberg

[57] ABSTRACT

Microspheres, of controllable shape and size, encapsulating active ingredients, are made by the internally controlled gelation of an emulsion including a water-soluble polysaccharide, a salt of a di- or trivalent metal cation, a polymerization inhibitor, water, a water-immiscible solvent (as a non-aqueous phase), and the active ingredient. The components of the aqueous phase, containing the water-soluble polysaccharide, polymerization inhibitor, di- or trivalent metal salt, active substance, and water, are blended together. This aqueous phase is then gradually mixed with the oil phase and agitated to form an emulsion. After sufficient time for solidification, the emulsion is broken and the resulting microspheres are collected. The active ingredient may be various substances, including live microorganisms.

19 Claims, 1 Drawing Sheet

INTERNAL GELATION METHOD FOR FORMING MULTILAYER MICROSPHERES AND PRODUCT THEREOF

BACKGROUND OF THE INVENTION

1. Field of the Invention

This invention relates generally to the formation of microspheres, and more specifically to the formation of microspheres by gelation.

2. Description of the Background Art

Over the past twenty years, the use of immobilized enzymes as catalysts for industrial, analytical, and medical purposes has been rapidly developed. This rapid development has occurred for the following reasons: (1) immobilization facilitates recovery and reuse of biological materials permitting continuous production; (2) processing of the immobilized whole cell or enzyme is easy; (3) activity is often markedly stabilized by immobilization that allows for repetitive use of a single batch of enzyme or cells; (4) improved control of the immobilized enzyme or whole cells and the ease of product removal often leads to higher yields and product purity.

The removal of hydrocarbon contaminants from soil presents one area where bioremediation using entrapped living cells is desirable. Present hydrocarbon removal methods often leave hydrocarbon contaminants in small pores in the contaminated soils. The introduction into the soil of hydrocarbon-degrading microorganisms, in a form that facilitates handling, storage, and controlled release, can remove these remaining traces of hydrocarbon contaminants. Entrapped microorganisms can also be advantageously used in soil fertilization and pest control.

Entrapment involves the polymerization of polyelectrolytes by multivalent ions and is one of the most common methods in whole cell immobilization. The ionic network formation procedure was first developed by Thiele and coworkers (Thiele, H. et al., *J. Biomed. Mat. Res.*, 3, 431, 442 (1969)) and the first example of whole cell immobilization through this method was reported by Hackel et al., *Eur. J. Appl. Microbiol.*, 1, 291–293, 1975. Currently, calcium alginate is the most popular matrix for whole cell immobilization. Entrapment within calcium alginate beads is considered a safe, simple, and economical system with good mechanical stability (Kennedy et al., *Appl. Biochem. and Bioeng.*, ed. by L Chibita et al. (Academic Press) vol. 4, pp 215–227 (1983). Because entrapped materials are surrounded by a polymeric shell, they are generally protected for some time against many environmental threats.

However, mixing and oxygen transfer problems arise in the inner core of beads having outside diameters of 1 mm or more. These limitations seriously impede the high productivity of calcium alginate beads including whole living cells.

U.S. Pat. No. 4,053,627 describes the use of alginate gel discs to release juvenile hormone into an aqueous environment. This process requires an essentially water-insoluble calcium salt with alginate, and then adding the salt/alginate mixture to water. This calcium salt is described as being insufficient to cause gelation of the alginate on an immediate basis. Further the reported process is slow, requiring up to 2 hours to complete gelation. This patent does not teach a method to produce microspherical particles for the entrapment of live cells, or microbes, nor does it include information on secondary means of controlling the gelation process.

U.S. Pat. No. 4,400,391 describes the use of alginate beads to entrap a range of bioactive materials. It describes a process by which the active agent is added to the sodium alginate. To facilitate gelation, the alginate/active agent mixture is then dropped from a suitable device into water containing a calcium salt. This patent claims that the size can be controlled in the range of 0.1 to 6 millimeters. Because this method adds a mixture of alginate and active ingredient to a calcium salt solution that causes gelation by diffusion into the bead, it would expose osmotically sensitive enzymes or live cells or microbes to unacceptably high concentrations of salts. This exposure would result in lower viability. In addition, the patent teaches away from the use of an internal set system to form particles containing the active compounds.

U.S. Pat. No. 4,822,534 teaches a method of forming microspheres by use of a water-in-oil emulsion system. This system also teaches the addition of calcium salts to break the emulsion or the addition of an organic acid such as acetic acid to the oil phase of the emulsion to permit gelation to occur. In that method, microspheres must be set from an external source by diffusion. This requirement is troublesome because microstructures are often coated by a layer of oil. This layer of oil hinders diffusion of the water-soluble salt to the sodium alginate, resulting in uneven gelation in an external set gelation system. Because of this uneven gelation, the microstructures undergo gross distortion. When gelation is initiated by an organic acid, the surface of the alginate polymerizes almost instantly, resulting in misshapen microstructures and exposure of live organisms to the acid, or pH labile chemicals to denaturation.

In scientific papers by Stormo and Crawford, Shao and Stevenson and Sheu and Marshall, microencapsulation by atomization into a salt solution is chosen as the preferred technique. Such methods use highly water-soluble salts to form microbeads either by dropping the sodium alginate into calcium chloride or by atomizing the sodium alginate and bacteria into the salt solution. The work of Stormo and Crawford indicates that high loadings of cells clog the atomization tip. Further, the method of Stormo and Crawford does not avoid rapid changes in osmolarity or pH. Reported techniques that use simple systems, relying on slowly dropping the polysaccharide result in very large spheres. Such spheres are not suitable for soil injection or use in other delivery methods that are size sensitive. Additionally, the literature indicates that gases may not sufficiently diffuse into to microbeads to support the viable microorganisms located more than 200–300 microns from the skin of the microstructure.

Further, with large diameter beads formed by dropping methods diffusion, kinetics through the beads by the divalent cations used to polymerize the alginate results in non-homogeneous polymerization due to the lack of control of the diffusional process. With polydispersed beads, this non-homogeneity makes it difficult to control the setting time for the alginate. As a result of this inability to control the alginate setting time, live cells may be exposed to excessive amounts of cationic salts for prolonged time periods, causing excessive cell death. A further problem is that the beads often do not exhibit good spheronization, since the outer shell of alginate sets on an immediate basis and does not allow the microstructures to become sufficiently spherical, resulting in uneven diffusional patterns.

SUMMARY OF THE INVENTION

Accordingly, it is an object of this invention to produce beads containing entrapped substances.

It is another object of the present invention to produce beads, of a controllable size and spherical shape, containing entrapped, viable microorganisms.

It is a further object of the present invention to produce microbeads containing entrapped, viable microorganisms, which may be dried without significant loss of viability.

These and additional objects of the invention are accomplished by the internally controlled gelation of an emulsion including a water-soluble polysaccharide, a salt of a di- or trivalent metal cation, a polymerization inhibitor, water, a water-immiscible solvent (as a non-aqueous phase), and an active ingredient. The water-soluble polysaccharide, polymerization inhibitor, di- or trivalent metal salt, active substance, and water, are first blended together. The resulting aqueous phase is then gradually mixed with the water-immiscible solvent (typically a fatty oil) under vigorous agitation. After sufficient time for solidification of the polysaccharide beads, the emulsion is broken and the resulting beads collected.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DESCRIPTION OF THE PREFERRED EMBODIMENTS

Figure 1:
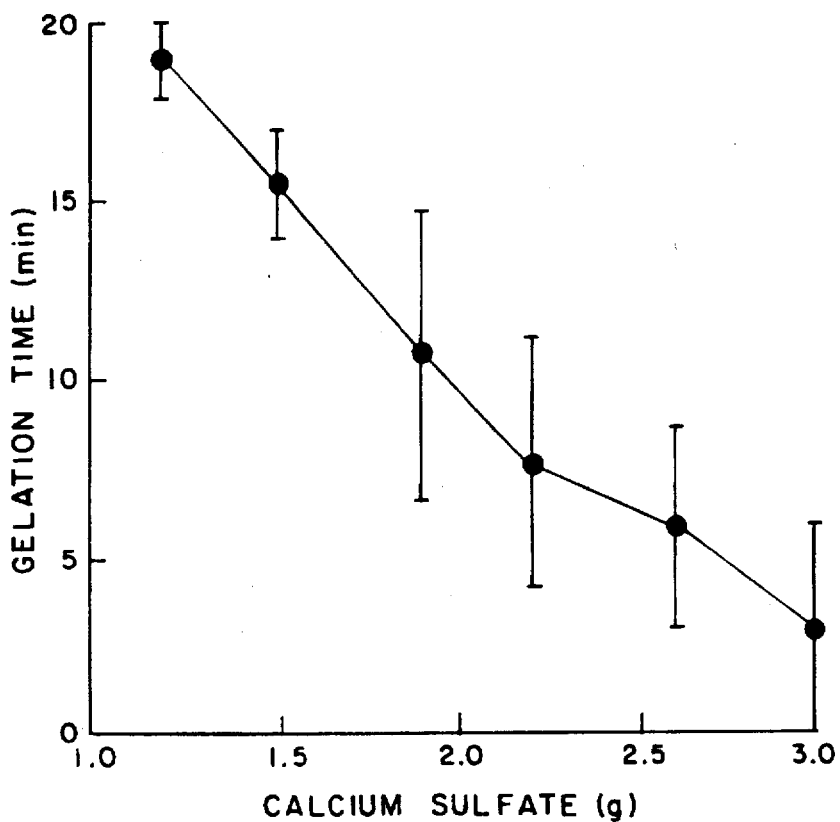
FIG. 1 is a graph of calcium alginate gelation time versus calcium sulphate mass added to the aqueous phases (110 ml) at a constant mixing speed of 420 rpm. The polyphosphate mass added to the aqueous phase was kept constant at 0.6 g for all time points.

Any water-soluble polysaccharide that polymerizes in the presence of a di- or trivalent metal salt may be used as the water-soluble polysaccharide component of the beads made according to the present invention. Typical polysaccharides useful in the present invention include sodium alginate (hydrated) and gellan gum. One particularly useful polysaccharide is Keltone LV®, a product of Kelco Division of Merck and Co., Inc. having a mesh size of 150, a viscosity of 250 cp in a 1% solution at a neutral pH when measured on a Brookfield LVF viscometer at 60 rpm and 20° C. with an appropriate spindle. The concentration of polysaccharide typically ranges from about 0.5 to about 4%, more often about 1.0 to about 3%, and most often about 1.2% to about 2%, by weight of the total aqueous phase.

The metal salt that causes polymerization of the polysaccharide is typically a salt of a di- or trivalent metal cation. Preferably, the salt has at least limited solubility in water.

Typical metal cations useful as gelling agents for polymerizing the polysaccharide in the present invention include cations of barium, lead, copper, strontium, cadmium, calcium, zinc, nickel, and aluminum. A mixture of these cations, in salt form, may also be used. The choice of the polymerizing compound will have an effect on polymerization properties and possibly on the release rate of the any substance dispensed in the polysaccharide bead. Typically useful di- or trivalent cation metal salts include chlorides, sulfates and acetates of calcium, barium, and copper. It may be useful to include a polyhydric alcohol, such as a glycol (e.g., ethylene glycol or propylene glycol) to enhance the water solubility of the metal salt.

The polymerization inhibitor may be any water-miscible substance that significantly slows the polymerization of the polysaccharide by interfering with the action of the gelling agent. These polymerization inhibitors may act, for example, by preventing binding of the metal cation of the gelling agent to the polysaccharide (as in the case of inhibition by sodium polyphosphates) or by sequestering the metal cation of the substrate, as in the case of a chelating agent, e.g., EDTA (ethylenediaminetetraacetic acid) and alkali metal salts thereof.

The entrapment system of the present invention is suitable for the retention of live cells, live microbial cells or spores, bacteria, yeasts or yeast spores, biologically active chemicals or enzymes, dyes, inks or flavorants or fragrances. Once formed, these microspheres are capable of inclusion in soils or sediments, food products, or cosmetic/pharmaceutical products or industrial process applications. Typically, the loading of the encapsulant (i.e., active agent) is from about 0.1% to about 50% by weight with respect to the initial alginate/water solution. More often, the loading of the encapsulant is from about 0.5% to about 35% by weight with respect to the initial alginate/water solution. Most often, the loading of the encapsulant is from about 1% to about 20% by weight with respect to the initial alginate/water solution.

Any oil may be used as the water-immiscible solvent for the non-aqueous phase. Preferably, the oil is environmentally safe. Generally, to facilitate the emulsification process, the oil is liquid at room temperature. Typical useful oils include vegetable oils such as corn oil, rapeseed oil, safflower oil, cottonseed oil, canola oil, peanut oil, other fatty oils, and mixtures thereof. Mineral oils may also be used, but may present a potentially greater environmental concern.

To form the microbeads, the water-soluble polysaccharide is blended into water to form the basis for the aqueous phase. The polysaccharide, usually a fine powder, is slowly blended into water (to which the di- or trivalent metal salt has been previously added) using either a very high speed shear pump, a high speed paddle mixer, or other agitation means sufficiently vigorous to fully wet the polysaccharide. Once the polysaccharide is fully wetted, the active agent is added. The second component of the aqueous phase is then blended. This second component includes the dispersing agent (for example, glycerol, propylene glycol, or another suitable polyol) (where a dispersing agent is present), water, and the polymerization inhibitor. When fully dispersed, the resulting mixture (hardening agent) is blended into the primary phase to form the polysaccharide mixture, i.e., the complete aqueous phase of the system. Blending the polysaccharide mixture in the above manner optimizes the dispersion of all components prior to the initiation of crosslinking by the cation. Although all components could be mixed simultaneously, sufficient time would need to be allowed to permit spheronization in an emulsion phase.

The resulting blend is then transferred to an emulsion-forming device which vigorously mixes the aqueous phase (i.e., the polysaccharide mixture) with the non-aqueous phase. The rate at which the polysaccharide mixture is added to the non-aqueous phase, the force and rate of mixing of the aqueous phase with the non-aqueous phase, and the viscosity of both phases, are controlled to assure that complete emulsification occurs before the onset of gelation. Significant gelation before the complete emulsification noticeably hampers the ability of the present invention to control the formation of microspheres.

Once the microspheres have hardened, the emulsion is broken, for example, by the addition of an aqueous solvent such as water. The formed microspheres may then be collected, for example, by filtration, or by allowing the microbeads to settle and decanting the liquid. The time required for hardening may be determined empirically, without undue experimentation. For example, the emulsion in test batches may be broken at various times, the beads collected, and their hardness determined.

The size of the polysaccharide microspheres may be controlled by the initial viscosity of the aqueous phase including the polysaccharide, the initial viscosity of the non-aqueous phase, and the energy applied to the emulsion (controlled in part by the rate of addition of the two phases together and by the force applied during mixing). Higher viscosity of the aqueous phase containing the polysaccharide, lower viscosity of the non-aqueous phase, and lower energy applied to the emulsion, result in a distribution of microspheres having a larger mean size. Low viscosity polysaccharide mixtures, more viscous oils, and higher energies applied to the emulsion, result in a distribution of microspheres having a smaller mean size.

The ratio of aqueous phase:non-aqueous phase should be sufficient to form an o/w/o emulsion. Typically, the ideal volume ratio of aqueous:non-aqueous phase is about 1:2–1:3.

Gel strength in the above system is governed by quantity of sequesterant used, the amount and type of the calcium source used, the type and quantity of entrapped materials, and use of large amounts of dispersants. If too high a concentration of dispersant is used, the phases will not segregate. If the concentration of dispersant is small, the size of the polysaccharide beads will be reduced. Typically, the concentration of the dispersant will be about 0.25%–5% by weight of the aqueous phase. In addition, the initial concentration of the polysaccharide can alter the viscosity of the aqueous phase, thus determining the gel properties to some extent.

Optionally, a surfactant may be added to either phase to aid in emulsification. Where live cells are to be entrapped within a microsphere, the surfactant should be non-toxic to those cells at the concentration used. Surfactants useful in the present invention include, but are not limited to, soy lecithin, polyoxyethylene ethers such as Brij™ (made by Sigma Co.), polyoxyethylene sorbitan fatty acid esters such as Tween™ (made by Sigma Co.), or sulfated oxyethylated alkylphenols such as Triton™ (made by Sigma Co.). Generally, microsphere size decreases with increasing surfactant concentration.

Typically, microspheres according to the present invention have diameters of from about two microns to greater than about 1000 microns depending on the initial viscosity of the aqueous phase including the polysaccharide, the initial viscosity of the water-immiscible (i.e., non-aqueous) phase, the type and amount of surfactant used in either the aqueous and/or non-aqueous phase. Although the present invention can also provide microspheres of at least about 1 or 2 mm diameter, microspheres larger than about 1000 microns may have diffusion characteristics that mitigate against the entrapment of viable cells.

In most cases, microspheres undergo syneresis or water loss upon gelation. Gelation increases the density of the microspheres, causing them to sink in water. The sinking of the gelled microspheres in water allows them to easily separate from the emulsion. This separation occurs when the emulsion is broken, for example by the addition of water. Typically, the polysaccharides are allowed to fully gel (fully harden) before the emulsion is broken.

If the polysaccharide-containing aqueous phase and the non-aqueous phase are either rapidly vortexed or pumped together through a high shear pump, a small amount of oil may be entrained in the polysaccharide microbeads. This small amount of oil will cause the microbeads to float in an aqueous environment. The microspheres of the present invention may be further modified by the addition of fillers, such as phospholipids, clay, calcium carbonate, synthetic and natural gums, chitosan, or synthetic polymers.

Having described the invention, the following examples are given to illustrate specific applications of the invention including the best mode now known to perform the invention. These specific examples are not intended to limit the scope of the invention described in this application.

EXAMPLES

Example 1

To 97 grams of water were added 0.5 g of sodium polyphosphate, and 3 grams of Keltone LV sodium alginate while rapidly mixing. In a separate container 3.0 grams of calcium sulfate were mixed with 5 grams of glycerol until the calcium sulfate was thoroughly wetted and dispersed. The mixing chamber was charged with 300 ml of soy vegetable oil and 15 grams of 90% soy phosphatidylcholine lecithin. These were then mixed until thoroughly blended. The calcium/glycerol mixture and the sodium alginate were then mixed together and immediately poured into the oil mixture to form an emulsion. The emulsion was vortexed for 10 minutes. After the 10 minutes of vortexing, an additional 300 milliliters of water was added to the emulsion to break the emulsion. Agitation of the emulsion was then stopped. The microspheres were than allowed to separate from the oil. This separation was possible because syneresis observed during gelation excluded water from the resulting microspheres, causing them to sink. The microspheres were then separated from the broken emulsion. Following separation from the aqueous phase, the oil could be reused.

Example 2

Alginate microspheres were formed as in Example 1 but using live bacteria at 10 g per 100 ml of the alginate solution, added following the hydration of the sodium alginate.

Example 3

Alginate microspheres were formed as in Example 1 but including a dye at the rate of 1% by weight of the alginate mixture, the dye added to the mixture prior to the calcium sulfate.

Example 4

Alginate microspheres were formed as in Example 1 and Example 2 except that a mixture of 1 gram gellan gum, 0.5 g of sodium citrate blended in 50 ml of distilled water were blended with the microbes prior to addition.

Example 5

Alginate microspheres were formed as in Example 1, except that the microbes were suspended in equal volumes of nutrient agar at 40° C., and the alginate solution was maintained at this temperature prior to blending. The oil phase was maintained at 30° C.

Example 6

Alginate microspheres were formed as in Example 1 and Example 2 except that following recovery from the emulsion phase, the microspheres were suspended in a 0.25% by weight mixture of sodium alginate and stirred at a speed just sufficient to prevent settlement for a period of 20 minutes to overcoat the microspheres with a layer of cell free alginate.

Example 7

Alginate microspheres were formed as in Example 1, except that following formation they were suspended in a 0.5% by weight solution of Chitosan for 20 minutes to bind the chitosan to the surface of the microspheres, followed by filtration and rinsing to remove excess unbound chitosan and then suspended in a water bath at pH 7.5–8.0 to render the chitosan insoluble.

Example 8

Alginate microspheres are formed as in Example 1 except the gellan gum was substituted for the sodium alginate.

Example 9

Alginate microspheres were formed as in Example 1 except that they were freeze-dried to a powder state. The beads were very lightweight, hard and retained their spherical shape.

Example 10

Alginate microspheres were prepared as in Example 2, except that they were freeze-dried to a powder state. Following reconstitution, regrowth of bacteria from the microspheres was observed.

Example 11

Alginate microspheres were prepared as in Example 1, except that a brewer's yeast suspension was added to the alginate prior to formation.

Example 12—Bacterial Encapsulation and Viability

Materials

Sodium Alginate Keltone LV was obtained from Kelco, Inc (Clark, N.J.). Calcium sulfate anhydrous, sodium polyphosphate and calcium chloride and sodium citrate were purchased from Aldrich (Milwaukee, Wis.). Glycerol, lauria agar and lauria broth base were obtained from Life Technologies Ltd. (Gaithersburg, Md.). Canola oil was purchased as a food grade product from a local grocery store. And *Achromobacter sp.* (ATCC 21910) was obtained from the American Type Culture Collection (Rockville, Md.). Tris base, sodium chloride and YES buffer were purchased from Sigma Chem Co. (St. Louis, Mo.).

Methods

Culture Conditions:

*Achromobacter sp.* was cultured in nutrient broth (L broth) in a rotary shaker (60 rpm) at 25° C. for 1,2,5,9 or 11 days to a final concentration of ca. $10^7$ CFU $ml^{-1}$. The bacterial culture (500 ml) was then centrifuged at 2000 rpm for 25 minutes. The pellet was resuspended in 40 ml of the desired medium (L broth or yeast extract salt "YES" buffer).

Bacterial Entrapment:

The bacterial encapsulation procedure was based on a biocompatible water/oil emulsification method for alginate microsphere preparation, developed previously. Sodium alginate (3% wt/vol) was blended in distilled water for 30 min. to ensure complete alginate hydration. This solution was then degassed to remove entrapped air bubbles for 60 min prior to use. For each 40 ml batch of the sodium alginate 0.2 g of sodium polyphosphate was added as a sequesterant prior to addition of the calcium source or bacterial slurry.

The organic phase of the emulsion was composed of canola oil to which 0.1% by weight of a mixed soy lecithin was added as an emulsifier. The organic/aqueous phase was kept constant at a ratio of 3:1 by volume. The oil phase was mixed at 3000 rpm for 5 min prior to emulsification.

During this mixing phase 2.5 g of a dry calcium sulfate powder was sonicated in 10 ml of a 50% glycerol solution to disperse and wet the calcium sulfate prior to addition to the alginate dispersion. The calcium sulfate suspension and bacterial slurry were then rapidly blended into the sodium alginate solution. A few drops of the mixture were set aside in a weight dish as a polymerization indicator and the remainder was added slowly to the oil phase.

Polymerization times were found to vary between 15–30 min, depending on the type of bacterial medium mixed into the alginate phase, prior to emulsification. The time taken for the emulsion to polymerize was assumed to be the same as for the retained indicator batch.

Emulsification was stopped by the introduction of 400 ml of water into the reactor while stirring continued. After about 10 minutes the stirring was stopped and the calcium alginate microspheres were allowed to fully precipitate to the bottom of the reactor vessel as the water and oil phases separated. Approximately 30% of the microspheres were found to remain at the interface of the oil and water phase and could be further separated by repeated washing with distilled water. Next the beads were washed at least twice in distilled water prior to storage at 4° C.

Viability: Determination by plate counts

A crude measure of bacterial viability in the microspheres is the ability of the entrapped bacteria to form colonies when added to nutrient media. Here, entrapped bacterial release was achieved by depolymerization of the calcium alginate microspheres by suspending them in sodium citrate buffer. After appropriate dilution in Tris Buffered Saline (TBS), the bacterial suspension was plated on to agar plates at 25° C. for 48 hrs. It was assumed that an individual colony was the result of a single viable cell, and the bacterial population was thus enumerated in colony forming units (CFU). this approach was then used as a conservative estimate of the initial bacterial concentration in the microspheres of the calcium alginate.

Lyophilization:

Lyophilization experiments were performed after a storage period of 24 hours, post entrapment. Typically 1 ml of the microsphere suspension was poured into a lyophilization bottle and plunged into liquid nitrogen for 10 min before pumping down in the freeze drying unit. For samples where trehalose was present, the supernatant was replaced with a trehalose solution at a final concentration of 50 mM. In cases where glycerol was used for bacterial protection the glycerol was added directly to the aqueous phase at a final concentration of 30% by volume prior to emulsification.

Basal Medium Preparation

A yeast extract salt (YES) medium was prepared by a stepwise combination of 4 stock solutions (18) indicated in Table 1. Stock solution A was added to 970 ml of distilled water. Purified agar (BBL, Cockeysville, Md.) was added (1.5% wt/vol) when a solid medium was desired. This solution was steam sterilized (121° C., 20 min) and allowed to cool to 50° C. To the cooled solution A, 10 ml of filter sterilized solution B. One ml of a filter sterilized solution C and 2 ml of D were then added with mixing. It is important to follow this sequence, temperature and mixing schedule to prevent formation of insoluble phosphates.

TABLE 1

Components of YES culture medium

Solution A: (50 × concentrate)

| | |
|---|---|
| K$_2$PO$_4$ | 58 g |
| KH$_2$PO$_4$ | 25 g |
| dH$_2$O | to 1000 ml |

Solution B: (100 × concentrate)

| | |
|---|---|
| MgSO$_4$ 4H$_2$O | 50 g |
| dH$_2$O | to 1000 ml |

Solution C: (1000 × concentrate)

| | |
|---|---|
| MnCl$_2$ 4H$_2$O | 2 mg |
| CuCl$_2$ 2H$_2$O | 28 mg |
| ZnCl$_2$ | 22 mg |
| CoCl$_2$ 6H$_2$O | 40 mg |
| Na$_2$MO$_4$ 2H$_2$O | 50 mg |
| FeCl$_2$ 6H$_2$O | 50 mg |
| dH$_2$O | to 1000 ml |

Solution D: (500 × concentrate)

| | |
|---|---|
| Diffco Yeast Extract | 5 g |
| dH$_2$O | to 500 ml |

Results

Initially, the effect of experimental artifacts such as buffer conditions on microsphere lysis was examined. Table 2 summarizes the effect of citrate buffer pH and concentration on the viability of entrapped bacteria. High levels of bacterial viability were observed under all conditions, suggesting that the citrate buffer was essentially harmless at the concentrations and pH used. However, the highest viability counts were observed at 250 mM citrate buffer at pH 4.0 and 10 mM citrate buffer at pH 6.0. The latter buffer conditions were adopted for subsequent experiments.

TABLE 2

Effect of citrate concentration and pH on viability

| | CPU (10$^7$ ml$^{-1}$) Citrate Buffer Concentration | | |
|---|---|---|---|
| pH | 10 mM | 50 mM | 250 mM |
| 2.5 | 4.0 | 2.3 | 2.0 |
| 5.0 | 2.0 | 2.0 | 1.9 |
| 6.0 | 2.5 | 2.1 | 1.9 |

Bacterial interaction and competition for available nutrients increased with cell concentration. This in some cases could have resulted in cell death following entrapment. Thus, the effect of initial bacterial abundance on subsequent cell viability following entrapment was examined (Table 2). Dilution of the initial concentration of bacteria by 10 and 20 fold did not result in statistically higher colony counts (CFU 10$^7$ ml$^{-1}$) and the bacterial interactions at initial concentration did not reduce entrapped cell viability. It should be noted that as shown in Table 2, storage of microencapsulated bacterial up to 15 days resulted in only a 3 fold lower viability. These results imply that the entrapped bacteria may be stored up to 15 days at 4° C. without significant loss of viability.

The influence of metabolic parameters such as the growth phase of the bacteria and their nutritional state prior to encapsulation on the ultimate recovery of viable CFUs was also examined. As shown in Table 3, viability counts for early and late stationary phase were at least an order of magnitude higher than those corresponding to the exponential phase. The highest encapsulation efficiency was found to be 40% for the early stationary phase, which is slightly higher than typical encapsulation efficiencies (30%) observed in the studies. It should also be noted that although storage of entrapped bacteria up to 4 days at 4° C. resulted in 3 fold lower colony counts relative to day 1 for all cases, the cells entrapped at early stationary phase remained the most viable.

TABLE 3

The effect of growth state on cell viability following 1 and 4 days storage at 4° C.

| Initial Culture | CFU (10$^7$ ml$^{-1}$) | |
|---|---|---|
| Growth Phase | Day 1 | Day 4 |
| EXPONENTIAL | 774 (114) | 272 (20) |
| EARLY STATIONARY | 3000 (800) | 860 (120) |
| LATE STATIONARY | 550 (150) | 220 (3) |

Table 4 examines the effect of bacterial incubation in YES buffer and L broth for different storage periods prior to the entrapment process. These effects indicate that bacterial viability is completely diminished after 11 days of incubation in the L broth. Surprisingly, although the viability of cells stored in YES buffer was reduced from 162·10$^7$ ml$^{-1}$ to 8·10$^7$ ml$^{-1}$ after 5 days, it did not diminish to zero by day 11. Rather, the viability was enhanced 7 fold as a result of possible fragmentation or division of the bacteria into smaller cells, due to bacterial adaptation to lower nutrient conditions.

TABLE 4

Effect of preincubation in L broth vs. YES buffer

| | CFU (10$^7$ ml$^{-1}$) | |
|---|---|---|
| Storage Time | YES | L broth |
| Day 1 | 162 (20) | 70 (22) |
| Day 5 | 8 (2) | 21 (2) |
| Day 11 | 55 (2) | 0 (0) |

In Table 5, the effect of lyophilization, as a means of preservation and storage, on the viability of entrapped Achromobacter sp (CFU ml$^{-1}$) is shown. As can be observed, high viability counts in all cases were observed; however, the highest viability was obtained when a 30% (vol %) solution of glycerol was added to the aqueous phase, prior to emulsification. Also it is interesting to note that the addition of trehalose, a synthetic sugar, to the supernatant prior to lyophilization has a protective effect on cell death as can be observed by higher colony counts (228·10$^7$ CFU ml$^{-1}$) obtained relative to that of the control at (144·10$^7$ CFU ml$^{-1}$).

TABLE 5

Summary of rehydrated entrapped colony counts

| Preservative | CFU (10$^7$ ml$^{-1}$) |
|---|---|
| Glycerol (30%)[a] | 324 (88) |
| Trehalose[b] | 228 (28) |
| None | 144 (28) |

[a]Glycerol (vol %) was introduced to the aqueous phase before emulsification.
[b]Trehalose was added to supernatant at final concentration of 50 mM before lyophilization.

Discussion

In examining of the feasibility of calcium alginate entrapment technology and applying it for the specific application of in-situ remediation the critical issues are bacterial viability and the ability of specific strains of microorganisms to degrade specific contaminants. Primary considerations should be the ability to deliver the required number of viable cells to the remediation site in order to provide for rapid initial remediation, and secondly to provide sufficient degrading activity based on that initial inoculant to provide timely clean up of the contaminant. Although considerable numbers of articles have been published on the degradation efficiency of immobilized bacteria, little emphasis has been placed on the physiologic state of the bacteria prior to entrapment.

In this study, focus was placed on optimization of bacterial conditions prior to alginate entrapment process in order to maximize the recover of viable cells. In addition, acceptable means of the transport, storage and delivery of degrading bacteria for in-situ bioremediation were determined.

Alginates are known to depolymerize in the presence of complexants such as phosphate and citrate due to the loss of calcium. Although this property may be a disadvantage for some medical applications, it was taken advantage of in this study to facilitate bacterial enumeration. The fact that high viability's were retained under all citrate buffer conditions considered, suggests that the citrate depolymerization may be favorably exploited for future quantitative studies on alginate entrapment methods.

One of the variables in alginate entrapment optimization processes is the effect of initial bacterial abundance on subsequent viability of the entrapped cells. This is because the interaction and competition for available nutrients increases as bacterial concentrations increase. Lin and his coworkers determined the effect of initial bacterial concentrations on the viability of PVA encapsulated Pseudomonas sp. CRE7 and Paucimobilis EPA 505 (Lin. J. E., Mueller, J. G., Peperstreate, K. J., Lantz, S. E., and Pritchard P. H., (1993), *Progress Report*, Naval Research Laboratory, Washington, DC.). They observed that in all cases the encapsulated bacterial viability decreased by an order of magnitude for the initial concentrations considered ($10^9$ and $10^{11}$ CFU $ml^{-1}$). In the present study, bacterial viability following alginate encapsulation remained in the same order of magnitude as initial bacterial concentrations, indicating that the alginate entrapment method offers excellent efficiency.

Metabolic parameters such as growth state and nutrient conditions prior to entrapment may also influence the entrapped cell viability. Typically, exponentially growing cells may be more susceptible to changes in their microenvironment than the cells in stationary phase. In the case under study, cells in the early stationary phase survived the entrapment and subsequent storage better when contrasted to cells entrapped in other growth states.

An important criteria for the addition of an inoculum in-situ is the penetration of the cell through a porous matrix and into the contaminated zone to act directly to the target pollutant. The starvation technique for preparation of the bacterial inoculum, which was developed by other for Klebsiella pneumoniae and p-Nitrophenol-degrading bacteria, results in cells of a smaller size and higher numbers per unit volume. Those researchers observed that PNP degrading cells increased from $1 \cdot 10^7$/ml to $6 \cdot 10^7$/ml after 8 weeks of starvation. In the case under study, the starvation technique was applied to *Achromobacter sp.* prior to encapsulation. Although the starvation period used in the present study (11 days) was considerably shorter than the 8 weeks reported by those researchers, it appeared to be sufficient to increase the bacterial viability by an order of magnitude relative to the survival experienced by starvation to day 5. This effect may be the result of acclimation of the bacteria to the lower nutrient conditions within the alginate microspheres and to the fragmentation or division of bacteria into smaller starved cells more adapted to storage conditions. If indeed this is the case, then the smaller starved cells as entrapped should have a greater chance of transport into the surrounding soils.

It was interesting to note that the bacteria grown on L broth for 11 days indicated zero viability. Thus, the starvation technique may also be considered in cases where storage of bacterial suspensions prior to encapsulation becomes a necessity.

One of the most well known methods for bacterial storage is freeze drying or lyophilization. However, there are problems accompanying this process. For example freezing and rehydration often leads to cell death. Lyophilization experiments performed on lactic acid bacteria in the presence of sodium alginate have proved alginate to be a preservative for dried microbes. This may serve to explain high viability's ($144 \cdot 10^7$ $ml^{-1}$) observed in this study, where bacteria had been entrapped in an alginate matrix prior to lyophilization and subsequent rehydration. The combination of different cryo-preservatives such as glycerol/alginate and trehalose/alginate were even more successful than calcium alginate alone in retaining cell viability following the lyophilization/rehydration process. This suggests that the effect of individual preservatives should be complementary toward maintaining cell viability. Sugars such as trehalose are known to protect live cells against lyophilization, although glucose, lactose and sucrose do not appear as efficient as is the case with glycerol.

Example 13

Materials

Sodium alginate, Keltone LV, was from Kelco, Inc. (Carlton, N.J.). Calcium sulphate anhydrous and sodium polyphosphate $(NaPO_3)_n$ was purchased from Aldrich (Milwaukee, Wis.). Canola oil, peanut oil, and olive oil were obtained from a local grocery store. Glycerol and soy bean lecithin were from Bethesda Research Laboratories (Bethesda, Md.) and Cargill (Cheasapeake, Va.), respectively. Reagent-grade acetone, methanol, and chloroform were from Fisher Scientific Products (Pittsburgh, Pa.). The alginate-specific dye (Victoria blue) was a product of Sigma Chemical Co. (St. Louis, Mo.).

Methods

Sodium alginate was dissolved in 500 ml distilled water using a Waring™ blender to prepare daily a fresh stock solution (2% w/v) for emulsification experiments. After complete homogenization, the alginate solution was stored in a beaker for 60 min for degassing. A fixed volume (100 ml) of the degassed sodium alginate solution was poured back in the blender in which 0.6 g sodium polyphosphate was dissolved. Two drops of highly concentrated dye reagent were added to the alginate solution prior to emulsification in order to facilitate alginate detection and thereby particle mean diameter measurements under the light microscope.

Typically, 1.9 g calcium sulphate was weighed in a plastic weigh boat to which 10 ml 50% (w/v) of glycerol/water mixture was added. The presence of glycerol in the mixture resulted in the further dispersion and solubility of calcium sulphate. After complete mixing, the suspension was sonicated for at least 15 min in the weight boat in order to breakdown the large calcium sulphate particles. This slurry was then blended into the alginate solution immediately before introduction to the oil phase.

The emulsification process was initiated by slowly transferring the alginate mixture containing hydrated sodium alginate, sodium polyphosphate, and calcium sulphate into 300 ml canola oil that had been vigorously mixed for 5 min at the mixing rate of 420 rpm. The last drops of alginate mixture were poured into a clean weigh boat to be used as a sample for optimum gelation time estimation. The required time of alginate bead formation by emulsification was assumed to be the same as that measured for the solidification of the sample under observation. After the time period allowed for complete solidification of alginate beads, 500 ml fresh distilled water was added to the reactor contents while stirring, in order to break down the emulsion. The stirrer was stopped after 5 min and thereafter, the reactor and its contents were transferred to the refrigerator. The majority of the calcium alginate beads precipitated at the bottom of the reactor at 4° C. over a period of 2–4 h. However, there was a small population of the beads (⅓ vol. %) that stayed at the oil/water interface and had to be washed three times with large volumes (500 ml) of cold distilled water for complete sedimentation into the aqueous phase.

Batches with smaller mean diameters (50–200 μm) were obtained by addition of either 1.0 or 10.0 g purified soy bean lecithin as an emulsifying agent. In these cases, the emulsification agent was added to the oil phase and stirred at 700 rpm for 15 min prior to emulsification.

The data presented here demonstrate the mean ±SD of at least three identical runs by independent experiments.

Reactor configuration The emulsification process was performed in a 100 ml Tri-pour plastic beaker. The reactor contents were mixed at either 420 or 580 rpm with a Stedfast stirrer model LR41 B with a 19⅝₀-inch long, four blades, stainless steel stirring shaft with a 2⅜-inch diameter propeller obtained from Fisher Scientific Co.

Bead size estimation

After each batch preparation a population of 90–120 spherical alginate beads was examined under a light microscope (Reichart-jung, series 150) for the measurement of mean diameter.

Lecithin purification

Soybean cake was blended with a 10-fold excess of acetone in a higher shear mixer and the solubilized fatty acids and other acetone-soluble components were removed. This was repeated a minimum of three times to remove the majority of fatty acids and other contaminants. Following this step, the resulting mixture was blended with a 20:80 v/v chloroform/methanol mixture at least 10 times the volume of soy solids, and again blended in a high-shear mixer for 4 min to solubilize the lecithins. Following this step, the chloroform methanol mixture was filtered to remove the protein solids. The resultant crude soy lecithin and solvent mixture was put in a Buchler rotary evaporator at 60° C. for 8–10 h in order to remove excess solvent. Although after this treatment the solvent content of purified lecithin was not determined, it was expected to be minimal. This is because, in experiments where bacteria were trapped in beads made using the same emulsifier, the retained viability of the bacteria following entrapment within the alginate matrix using the lecithin extract as an emulsifying agent was basically the same as the starting bacterial suspensions.

The lecithin extract was of at least 95% purity, as determined by NMR. This crude extract was then employed as an emulsifier for the calcium alginate beads size reduction.

Results

FIG. 1 shows the relationship between total calcium sulphate (g) added to sodium alginate solution (110 ml) in the presence of polyphosphate sequesterant versus time of calcium alginate gelatin. Successful bead formation occurred within the time frame of 4–19 min depending on the concentration of a calcium source. It appeared that batches with a higher content of calcium sulphate precipitated faster than others, possibly due to a higher density of calcium alginate particles.

The gelation time was also controlled by addition of variable amounts of sodium polyphosphate as a sequesterant (Table 4). Concentrations of the calcium source and sodium alginate were kept constant at 1.9/110 (w/v) and 2% (w/v) respectively. The polymerization time varied between 5 and 35 min depending on the concentration of sequesterant.

Figure 2:
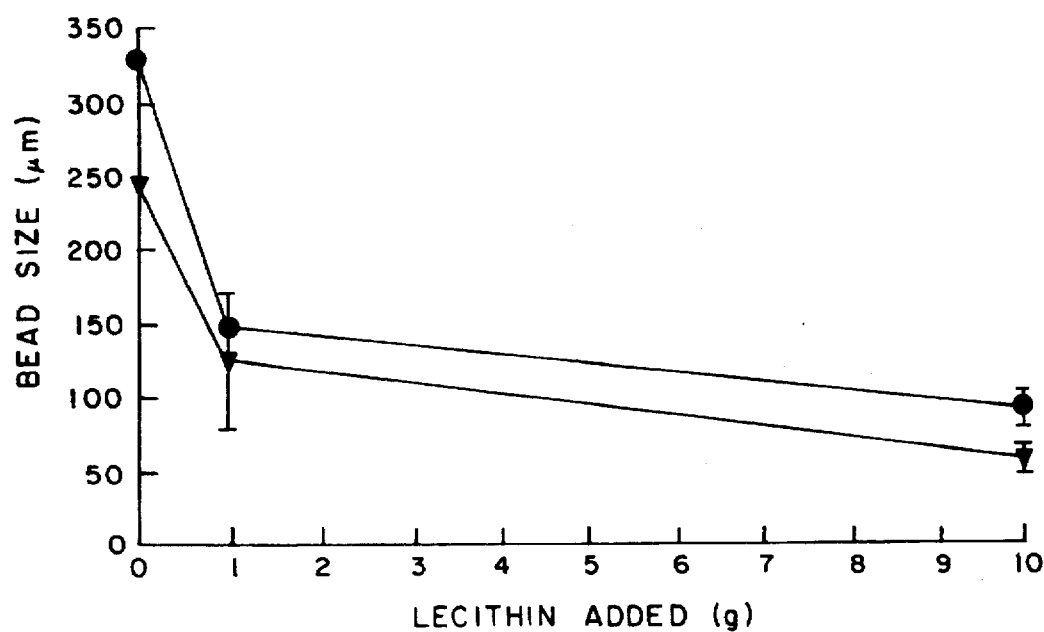
FIG. 2 is a graph of beads mean diameter (µm) versus purified lecithin mass added to the oil phase (300 ml) at (•) 420 rpm and (▼) 580 rpm. The mass of calcium sulphate and sodium polyphosphate added to the aqueous phase for both mixing speeds were 1.9 and 0.6 g, respectively.

The effective role of purified soy bean lecithin as an emulsifier for size control of calcium alginate beads is demonstrated in FIG. 2. As can be observed, the mean diameters of the beads at constant stirring speed (420 rpm) were reduced from 330 to 90 μm by increasing the mass of added lecithin. Further size reduction of the beads was achieved by increasing the speed of mixing at high concentrations of lecithin, which resulted in successful production of alginate beads of 56 μm mean diameter. Variation in the nature of the oil phase was also examined as a means of controlling the mean diameter of the fabricated beads. The mean diameter of the calcium alginate particles decreased from 330.3 (44.7) μm in the case of canola oil to 264.4(48.6) and 176.9 (26.2) μm for peanut and olive oil respectively.

Additional details concerning the present invention are described in Monshipouri et al., *J. Microencapsulation*, 1995, Vol. 12, No. 3, 255–262, the entirety of which is incorporated herein by reference for all purposes.

Obviously, many modifications and variations of the present invention are possible in light of the above teachings. It is therefore to be understood that, within the scope of the appended claims, the invention may be practiced otherwise than as specifically described.

What is claimed is:

1. A process for preparing polysaccharide microspheres having a diameter of about 2μ–1000μ by internally controlled gelation, comprising the steps of:

providing an aqueous phase by blending, in the presence of water, a first component with a second component, thereby forming an aqueous phase, said first component comprising a di- or trivalent metal salt in a concentration effective to significantly promote gelling of said polysaccharide in said aqueous phase, said second component comprising a water-soluble polysaccharide and a polymerization inhibitor for inhibiting the polymerization of said polysaccharide in a concentration effective to significantly inhibit the gelling of said polysaccharide in said aqueous phase, said first component or said second component further comprising an active substance, mixing, before significant gelation of said polysaccharide in said aqueous phase occurs, said aqueous phase with a non-aqueous phase with agitation to form an emulsion, in a ratio of said aqueous phase to said non-aqueous phase such that said emulsion is an o/w/o emulsion, said non-aqueous phase comprising a water-immiscible solvent, said emulsion comprising said active substance entrapped within polysaccharide microspheres having a diameter of about 2μ–2000μ;

allowing said polysaccharide microspheres, having said active substance entrapped therein, to gel, thus forming, in said emulsion, gelled microspheres having a diameter of 2μ–2000μ, said gelled microspheres having said active substance entrapped therein;

breaking said emulsion comprising said gelled microspheres to form a broken emulsion; and collecting said gelled microspheres from said broken emulsion.

2. The method of claim 1, wherein said emulsion comprising said gelled microspheres is broken by the addition of water thereto.

3. The method of claim 1, wherein said water-immiscible solvent is a fatty oil.

4. The method of claim 3, wherein said fatty oil is selected from the group consisting of corn oil, rapeseed oil, safflower oil, cottonseed oil, canola oil, peanut oil, and mixtures thereof.

5. The method of claim 1, wherein said first component is made by a process including the steps of:

forming an aqueous solution of said di- or trivalent metal salt in a concentration effective to significantly promote the gelling of said polysaccharide in said aqueous phase;

blending said polysaccharide, in powder form, into said aqueous solution of said di- or trivalent metal salt, while agitating said aqueous solution, until said aqueous solution fully wets said polysaccharide, thus forming a blend;

adding said active substance to said blend, thus forming said first component, and wherein said second component comprises includes water, said polymerization inhibitor in a concentration effective to significantly inhibit the gelling of said polysaccharide, and, optionally, a dispersing agent.

6. The method of claim 5, wherein said dispersing agent is a polyol.

7. The method of claim 6, where said dispersing agent is present in said aqueous phase at a concentration of about 0.25%–5% by weight of said aqueous phase.

8. The method of claim 1, wherein the active substance is a live microbial cell or a viable spore.

9. The method of claim 1, wherein the active substance is an enzyme or dye.

10. The method of claim 9, wherein the active substance is an ink.

11. The method of claim 1, wherein the active substance is a fragrance.

12. The method of claim 1, wherein the active substance is a flavorant.

13. The method of claim 1, wherein said active agent is present in said aqueous phase at a concentration of about 0.1%–50% with respect to the weight of said aqueous phase.

14. The method of claim 1, wherein said polysaccharide is selected from the group consisting of hydrated sodium alginate and gellan gum.

15. The method of claim 1, wherein said polymerization inhibitor is a sequesterant for said di- or trivalent metal salt or prevents binding of said di- or trivalent metal salt to said polysaccharide.

16. The method of claim 15, wherein said polymerization inhibitor is ethylenediaminetetraacetic acid, an alkali metal salt of ethylenediaminetetraacetic acid, or a sodium polyphosphate.

17. The method of claim 1, wherein the volume ratio of said aqueous phase to said non-aqueous phase about 1:2–1:3.

18. The method of claim 1, further comprising the step of adding a surfactant to said aqueous phase or said non-aqueous phase before forming said emulsion.

19. The method of claim 1, wherein the concentration of said polysaccharide in said aqueous phase is about 0.5–4% by total weight of said aqueous phase.

* * * * *